United States Patent [19]

Peters

[11] Patent Number: 4,459,173

[45] Date of Patent: Jul. 10, 1984

[54] PROCESS FOR ETCHING GLASS CAPILLARIES FOR CHROMATOGRAPHY

[75] Inventor: Thomas L. Peters, Midland, Mich.

[73] Assignee: The Dow Chemical Company, Midland, Mich.

[21] Appl. No.: 516,488

[22] Filed: Jul. 22, 1983

Related U.S. Application Data

[63] Continuation of Ser. No. 330,359, Dec. 14, 1981, abandoned.

[51] Int. Cl.$^3$ .................... B44C 1/22; C03C 15/00; C03C 25/06
[52] U.S. Cl. ........................................ 156/663; 65/31; 252/79.3; 252/79.4; 427/309
[58] Field of Search ............................ 65/31; 156/663; 252/79.3, 79.4; 427/230, 309

[56] References Cited

PUBLICATIONS

American Chemical Society, Dec. 1978, Etching and Deactivating Glass Capillary Columns for Gas Chromatography by R. Heckman et al., pp. 2157-2158.

*Primary Examiner*—William A. Powell
*Attorney, Agent, or Firm*—Burke M. Halldorson

[57] ABSTRACT

An improved process for etching (eroding) the inner surface of a glass capillary column in which ammonium bifluoride in liquid methanol is passed slowly through the capillary bore for a prolonged period, followed by rinsing with methanol, thereafter a gradually diluting rinse mixture of methanol and water, and finally a pure water rinse. A very fine structured etch of uniform depth is produced with no apparent air entrainment making the columns suitable for all standard stationary phase coating procedures.

4 Claims, No Drawings

PROCESS FOR ETCHING GLASS CAPILLARIES FOR CHROMATOGRAPHY

CROSS-REFERENCE TO RELATED APPLICATION

This is a continuation of application Ser. No. 330,359, filed Dec. 14, 1981, now abandoned.

FIELD OF THE INVENTION

The present invention relates to chromatographic column glass capillaries of the wall coated open tubular (WCOT) type in which the stationary liquid phase is present as a thin film supported on the inner surface of the capillary. More specifically, the invention relates to an improved process for uniformly matte-etching (eroding) the inner surface of a glass capillary column to prepare the surface for deactivation and coating with stationary phase for chromatography. The process results in a uniform and a fine structured etch without resorting to use of high temperature thermal reactions with, e.g., hydrogen fluoride gas.

BACKGROUND OF THE INVENTION

Glass capillary columns have become increasingly important for use in chromatography due to significant advantages over metal. Of particular analytical importance is the relative catalytic inertness of glass, especially for high temperature chromatography. It is known, however, that stationary phase coating procedures useful for metal capillaries seldom yield high efficiency glass capillary columns, or columns which are satisfactorily stable. To overcome these drawbacks, glass surface modifications and treatments have been extensively studied. Among these are surface roughening procedures which theoretically should yield greatly enhanced column efficiency and stationary phase film stability.

Among the closest of these prior art methods to the invention are those which use hydrogen fluoride reagent to attack the glass surface. In this respect, both gaseous and aqueous hydrogen fluoride have been used for surface roughening of glass capillary columns. Aqueous hydrogen fluoride, however, does not, as used in typical procedures, apply a matte-etch to borosilicate glass, and treatment of flint or soft glass capillaries by either gaseous or aqueous hydrogen fluoride is extremely difficult to control. These procedures, therefore, are not currently widespread in use.

A more commonly applied method is that which relies on the decomposition of ammonium bifluoride (or, e.g., a fluorinated ether) which is deposited in the capillary, the ends of the capillary sealed, and the capillary subsequently heated to 450° C. to generate hydrogen fluoride gas. This procedure causes what is referred to as "silica whisker" formations on the inner surface of the glass. The major shortcomings of this method remain a lack of satisfactory uniformity, frequently in the form of too severe an etch for chromatography purposes. In addition, the high temperature reaction with hydrogen fluoride gas poses severe potential hazards and must be approached with extreme care. This latter procedure, for more details, is described in some depth by Onuska, J. of Chrom., 142 (1977), pp. 117–125.

Yet another surface roughening procedure for glass capillaries for chromatography uses 10–20% aqueous potassium difluoride reactant which is added to the capillary bore, followed by rinsing with water to dissolve the reaction product ($K_2SiF_6$), thus producing an eroded or roughened surface texture. The resultant etch is often gradient in nature, however, and thus not satisfactorily uniform along the length of the column.

BRIEF SUMMARY OF THE INVENTION

A new technique has now been discovered for improved etching of glass (borosilicate and soft glass) capillaries for chromatography which overcomes the deficiencies of the prior art. It is both much safer to practice, being conducted typically at ambient temperatures, and also is highly controllable. It thus results in an extremely uniform and reproducible matte-etching of the inner surface of the capillary producing a surface with more ideal properties for depositing a stationary phase.

More specifically, the method of the invention for etching the inner surface of a glass capillary column for chromatography, and in preparation for deactivating and coating the inner surface of the capillary with stationary phase, comprises the combination of steps of:

(a) flowing through the bore of the capillary a liquid etching solution of ammonium bifluoride dissolved in methanol, (b) continuing step (a) for a sufficient time to produce a frosted surface, (c) thereafter adding a rinse solution of liquid methanol to the bore of the capillary, (d) without segmenting the flow of the rinse solution to the capillary, adding to the rinse solution water, thereby rinsing the capillary with a solution of liquid methanol mixed with water, and (e) without segmenting the flow of the rinse solution to the capillary, continuing to rinse the capillary bore using a rinse solution of essentially water until essentially complete extraction of the reaction product $(NH_4)_2SiF_6$ is obtained.

DETAILED DESCRIPTION OF THE INVENTION

Glass column capillaries for chromatography, which are prepared for such use by the inventive process, are generally between about 0.1–0.8 mm I.D. and from about 10–100 meters in length. They are suitably of borosilicate (Pyrex ®) or soda-lime (soft or flint) capillary glass stock.

A very important aspect of the invention in achieving a uniform matte-etch of the inner surface of these capillaries is the use of step (a) of the inventive process in which a self-limiting reaction of the glass is obtained by the selection of the proper etching reagent and its solvent. Because the reaction is of a self-limiting nature, it can be controlled and made highly uniform for the entire length of the bore of the capillary. The solvent selected is critically methanol most preferably having little or no dissolved water present. The liquid etching solution is prepared by dissolving preferably a saturated amount of ammonium bifluoride in the dry methanol solvent to prepare a solution of about 4% (w/v) ammonium bifluoride in methanol.

The etching solution is added, e.g, from a suitable reservoir from which it is pushed by nitrogen or other inert gas through the bore of the capillary. Preferably ambient temperatures are used, although elevated temperatures below the boiling point of the methanol carrier may be alternatively employed. Generally, about 3–7 column volumes of etching solution are pumped slowly through the capillary for a prolonged period, e.g., 5-15 hours at flow rates of typically about 1-10 ml/hr.

Etching by this process produces as the reaction product $(NH_4)_2SiF_6$ which is insoluble in methanol solvent and adheres to the glass surface, limiting further reaction with the etching solution; and thus limiting the depth of the reacted layer. Upon completion of step (a), the capillary exhibits a highly uniform and frosted surface of the entire length of the capillary bore (visible only in the dry capillary).

Following the etching step, the capillary is disconnected from the reservoir of etching solution, and connected preferably to a liquid chromatographic pump to complete the remaining rinsing steps (c)-(e). Apparatus for practicing these steps comprises preferably a mixing vessel suitably of about 40 ml volume. The mixing vessel is connected by a switching valve to reservoirs of water and methanol, respectively. In practicing step (c) of the process, the mixing vessel is filled with methanol which is pumped slowly, suitably at a rate of about 0.5-1.0 ml/min, through the capillary bore. Typically, about 3-10 column volumes of dry methanol are passed through the capillary for an initial rinse period of about 0.5 to 3 hours. The methanol removes essentially all residual ammonium bifluoride reactant without detrimentally disturbing the adhered layer of $(NH_4)_2SiF_6$. Without segmenting the flow of rinse solution to the bore of the capillary, the switching valve is manually turned to add water to the mixing vessel, and terminate the flow of methanol. A mixture of methanol and water is thus produced within the mixing vessel which gradually is diluted to pure water as the vessel is emptied, and additional water added. The water/methanol and later essentially pure water rinse gradually dissolves and dislodges the $(NH_4)_2SiF_6$ reaction product, which by the slow graduation from methanol to water in the rinse avoids capillary plugging with dislodged $(NH_4)_2SiF_6$ particles.

Generally about 3-10 column volumes of methanol/water mixture, followed by 3-10 columns of pure water are pumped slowly through the column to obtain essentially complete removal of the $(NH_4)_2SiF_6$ reaction product. Following completion of this step, and drying with purified nitrogen, a uniform fine matte-etch is evident in the form of an easily perceptible opaqueness. Although the etch is very fine structured, no problems with air entrainment have been encountered as with whisker columns making the columns suitable for all standard coating procedures.

PROCESS PARAMETERS

The term "without segmenting" means the avoidance of detrimentally introducing air bubbles into the rinse solutions which would cause capillary plugging. In this respect, particles of $(NH_4)_2SiF_6$ dislodge and move forward with the rinse solution. If an air bubble is present, the particles can collect and eventually can plug the capillary. Plugging can also occur if the transition from methanol to water is made too abruptly.

The critical properties of the methanol solvent used in the invention is solubility of a reactive amount of ammonium bifluoride, and relative insolubility to $(NH_4)_2SiF_6$; and for the rinsing steps, the further property of being a water miscible solvent. Inert solvents having the same functional properties could be mixed with methanol or substituted in the alternative to effectively practice the invention. These are intended to be covered within the broad scope of the claimed invention by application of the Doctrine of Equivalents.

The final rinse step with essentially water is preferentially practiced using pure water to insure that the $(NH_4)_2SiF_6$ reaction product is entirely removed from the capillary surface. The term "essentially water" means in the broadest sense that there is sufficient water in the rinse to accomplish this removal. The rinse solution if other than pure water may contain ingredients other than as would detrimentally prevent this extraction from being carried to essential completeness.

COLUMN DEACTIVATION AND COATING

Upon completion of the etching process, the capillary columns may be prepared for storage by rinsing with methanol, followed by methylene chloride, and drying with purified nitrogen. The column ends are then flame sealed to protect the column for prolonged storage.

Alternatively, the etched columns may be coated and used immediately for chromatography by deactivating and coating the inner bore of the capillary with stationary phase. These coating procedures are well known and usually preceded by acid leaching of the inner surface of the capillary with heated, concentrated hydrochloric acid, for a prolonged period, e.g., as described by Grob et al., Chromatographia, 10, 181-187. The columns may then be surface deactivated and coated with stationary phase by conventional methods. Highly efficient and thermally stable capillary columns prepared using the etching procedure of this invention, and coated using apolar and mixed apolar/polar stationary phase coatings, are described in detail by Nestrick et al., U.S. application Ser. No. 330,343, filed Dec. 14, 1981 and entitled "Coated Capillary Chromatographic Column", incorporated herein by reference (now U.S. Pat. No. 4,376,641).

EXAMPLE

A borosilicate capillary is first flushed with 5-column volumes of methanol followed by methylene chloride and then dried with purified nitrogen. Five column volumes of the etching solution (methanol saturated with ammonium bifluoride) are very slowly pushed through the column such that the total contact time is about 8 to 12 hours. The column is then rinsed with about 5-column volumes of methanol and about 5-column volumes of water/methanol solution according to the gradient rinse procedure described. A final rinse of about 5-columns of water is used for step (e) of the process, these rinse solutions being added slowly and without interruption over a prolonged rinse cycle of about 1 to 4 hours.

After drying, the etch is evident in the form of an easily perceptible opaqueness. A SEM photograph reveals the etch to be extremely uniform and fine structured. The depth of the etch ranges from 0.1 to 0.2 micron with a distance of ca 10 microns between "peaks".

What is claimed is:

1. A method for etching the inner surface of a glass capillary column for chromatography in preparation for deactivating and coating the inner surface of the capillary with stationary phase which comprises the combination of steps of:
   (a) flowing through the bore of the capillary a liquid etching solution of ammonium bifluoride dissolved in methanol, (b) continuing step (a) for a sufficient time to produce a frosted surface,
(c) thereafter adding a rinse solution of liquid methanol to the bore of the capillary,
(d) without segmenting the flow of the rinse solution to the capillary adding thereto water, thereby rinsing the capillary with a rinse solution of liquid methanol mixed with water, and
(e) without segmenting the flow of the rinse solution to the capillary, terminating the addition of methanol to produce a final rinse of the capillary wherein the rinse solution is essentially water.

2. A method for etching the inner surface of a glass capillary column for chromatography in preparation for deactivating and coating the inner surface of the capillary with stationary phase, which comprises the combination of steps of:

(a) flowing through the bore of the capillary a liquid etching solution of ammonium bifluoride dissolved in methanol,
(b) continuing step (a) for a sufficient time to produce a frosted surface,
(c) thereafter adding a rinse solution of liquid methanol to the bore of the capillary,
(d) without segmenting the flow of the rinse solution to the capillary, adding thereto water, thereby rinsing the capillary with a rinse solution of liquid methanol mixed with water, and
(e) continuing to rinse the capillary bore using a rinse solution of essentially water until essentially complerte extraction of the reaction product $(NH_4)_2SiF_6$ is obtained.

3. The method of claim 2 wherein step (e) comprises reducing or terminating the addition of methanol to produce a final liquid rinse solution of essentially water.

4. The method of claim 3 wherein the final rinse solution is essentially water undiluted with methanol.

* * * * *

UNITED STATES PATENT AND TRADEMARK OFFICE
CERTIFICATE OF CORRECTION

PATENT NO. : 4,459,173

DATED : July 10, 1984

INVENTOR(S) : Thomas L. Peters

It is certified that error appears in the above—identified patent and that said Letters Patent is hereby corrected as shown below:

Col. 3, line 10, delete the word "of", first instance, and insert the word --for--.

Col. 6, Claim 2, lines 14 and 15, delete "complerte" and insert --complete--.

Signed and Sealed this

Twenty-sixth Day of February 1985

[SEAL]

Attest:

DONALD J. QUIGG

Attesting Officer

Acting Commissioner of Patents and Trademarks